United States Patent [19]
Berg

[11] Patent Number: 5,658,436
[45] Date of Patent: Aug. 19, 1997

[54] SEPARATION OF 2-METHYL-1-BUTANOL FROM 3-METHYL-1-BUTANOL BY EXTRACTIVE DISTILLATION

[76] Inventor: Lloyd Berg, 1314 S. Third Ave., Bozeman, Mont. 59715

[21] Appl. No.: 730,030

[22] Filed: Oct. 15, 1996

[51] Int. Cl.$^6$ .................. B01D 3/40; C07C 29/84
[52] U.S. Cl. .................. 203/57; 203/63; 203/67; 203/68; 203/69; 203/70; 568/913
[58] Field of Search .................. 203/57, 67–70, 203/63–64; 568/913

[56] References Cited

U.S. PATENT DOCUMENTS

| | | | |
|---|---|---|---|
| 2,559,520 | 7/1951 | Smith, Jr. et al. | 203/64 |
| 4,732,653 | 3/1988 | Berg | 203/61 |
| 4,969,977 | 11/1990 | Berg | 568/913 |
| 5,401,366 | 3/1995 | Berg | 203/57 |
| 5,407,540 | 4/1995 | Berg | 203/58 |
| 5,407,541 | 4/1995 | Berg | 203/68 |
| 5,407,542 | 4/1995 | Berg | 203/68 |
| 5,417,813 | 5/1995 | Berg | 203/70 |
| 5,417,814 | 5/1995 | Berg | 203/63 |
| 5,439,561 | 8/1995 | Berg | 203/58 |
| 5,447,608 | 9/1995 | Berg | 203/69 |

FOREIGN PATENT DOCUMENTS

| | | | |
|---|---|---|---|
| 0047204 | 3/1982 | European Pat. Off. | 203/57 |

*Primary Examiner*—Virginia Manoharan

[57] ABSTRACT

2-Methyl-1-butanol is impossible to separate from 3-methyl-1-butanol because they both boil at 130° C. 2-Methyl-1-butanol can be readily separated from 3-methyl-1-butanol by extractive distillation. Effective agents are o-xylene, 3-carene and 1-methoxy-2-propanol.

1 Claim, No Drawings

SEPARATION OF 2-METHYL-1-BUTANOL FROM 3-METHYL-1-BUTANOL BY EXTRACTIVE DISTILLATION

FIELD OF THE INVENTION

This invention relates to a method for separating 2-methyl-1-butanol from 3-methyl-1-butanol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Methyl-1-butanol and 3-methyl-1-butanol both boil at 130 degrees C. and have a relative volatility 1.0 and are impossible to separate by conventional rectification. Table 2 shows that to get 99% purity with an agent giving a relative volatility of 1.55, only twenty-eight actual plates are required.

TABLE 2

Theoretical and Actual Plates Required vs. Relative Volatility for 2-Methyl-1-butanol-3-Methyl-1-butanol Separation

| Relative Volatilty | Theoretical Plates Required At Total Reflux, 99% Purity | Actual Plates Required, 75% Eff. |
|---|---|---|
| 1.2 | 49 | 65 |
| 1.45 | 24 | 32 |
| 1.55 | 21 | 28 |

OBJECTIVE OF THE INVENTION

The object of this invention is to provide a process or method of extractive distillation that will enhance the relative volatility of 2-methyl-1-butanol from 3-methyl-1-butanol in their separation in a rectification column. It is a further object of this invention to identify effective extractive distillation agents that are stable and can be recycled.

SUMMARY OF THE INVENTION

The objects of this invention are provided by a process for the separation of 2-methyl-1-butanol from 3-methyl-1-butanol which entails the use of certain organic compounds when employed as the agent in extractive distillation.

DETAILED DESCRIPTION OF THE INVENTION

I have discovered that certain organic compounds will effectively increase the relative volatility between 2-methyl-1-butanol and 3-methyl-1-butanol during rectification when employed as the agent in extractive distillation. Table 3 summarizes the data obtainied.

TABLE 3

Effective Extractive Distillation Agents For Separating 2-Methyl-1-butanol From 3-Methyl-1-Butanol

| Compounds | Relative Volatility |
|---|---|
| None | 1.0 |
| Ethyl benzene | 1.45 |
| o-Xylene | 1.55 |
| Limonene | 1.4 |
| Dipentene | 1.5 |
| 3-Carene | 1.5 |
| 2-Ethoxyethanol | 1.4 |
| 1-Methoxy-2-propanol | 1.5 |
| 1-Nitropropane | 1.3 |

The agents which are effective are ethyl benzene, o-xylene, limonene, dipentene, 3-carene, 2-ethoxyethanol, 1-methoxy-2-propanol and 1-nitropropane.

THE USEFULNESS OF THE INVENTION

The usefulness or utility of this invention can be demonstrated by referring to the data presented in Tables 1, 2 and 3. All of the successful agents show that 2-methyl-1-butanol can be separated from 3-methyl-1-butanol by means of extractive distillation and that the ease of separation is considerable.

WORKING EXAMPLE

Example 1: Fifty grams of 2-methyl-1-butanol - 3-methyl-1-butanol mixture and fifty grams of o-xylene as the extractive distillation agent were charged to a vapor-liquid equilibrium still and refluxed for three hours. The vapor composition was 56% 2-methyl-1-butanol and 44% 3-methyl-1-butanol; the liquid composition was 45.1% 2-methyl-1-butanol, 54.9% 3-methyl-1-butanol. This is a relative volatility of 1.55.

I claim:

1. A method for recovering 2-methyl-1-butanol from a mixture consisting of 2-methyl-1-butanol and 3-methyl-1-butanol which consists essentially of distilling said mixture in the presence of an extractive agent, recovering the 2-methyl-1-butanol as overhead product and obtaining the 3-methyl-1-butanol and the extractive agent as bottoms product, wherein said extractive distillation agent consists of one material selected from the group consisting of ethyl benzene, o-xylene, limonene, dipentene, 3-carene, 2-ethoxyethanol, 1-methoxy-2-propanol and 1-nitropropane.

* * * * *